United States Patent [19]

Heinemann et al.

[11] 4,007,052
[45] Feb. 8, 1977

[54] PREPARATION OF ADJUVANT-FREE FRUCTOSE TABLETS

[75] Inventors: Helmut Heinemann, Heidelberg; Werner Rothe, Hockenheim, both of Germany

[73] Assignee: Boehringer Mannheim G.m.b.H., Mannheim, Germany

[22] Filed: Aug. 1, 1975

[21] Appl. No.: 601,571

[30] Foreign Application Priority Data

Aug. 23, 1974  Germany .......................... 2440383

[52] U.S. Cl. ............................. 127/30; 106/38.22; 127/63; 264/39; 264/300; 424/180; 424/230; 424/269; 424/280; 424/298; 424/361

[51] Int. Cl.² ..................... B29C 1/04; C13K 11/00

[58] Field of Search ............... 264/39, 300; 127/30, 127/63; 106/38.22

[56] References Cited

UNITED STATES PATENTS

| | | | |
|---|---|---|---|
| 2,444,282 | 6/1948 | Creevy | 106/38.22 X |
| 3,060,511 | 10/1962 | Parmella | 264/300 X |
| 3,169,888 | 2/1965 | Ryan | 127/63 X |
| 3,305,447 | 2/1967 | Reimers | 127/63 X |
| 3,639,168 | 2/1972 | Monti | 127/63 X |

*Primary Examiner*—Morris O. Wolk
*Assistant Examiner*—Sidney Marantz
*Attorney, Agent, or Firm*—Burgess, Dinklage & Sprung

[57] ABSTRACT

The method of preparing adjuvant-free tablets from a tableting mass having a tendency to stick, comprising alternately in the same mold forming tablets from said tableting mass and from an adjuvant mass containing an easily tableted substance, a lubricant and a mold parting agent. The lubricant may be talc or sodium benzoate present in about 5 to 20% by weight, and the mold release agent may be stearic acid, a stearate, paraffin or a silicone oil in about 0.5 to 10% by weight. By this method tablets of pure fructose can be formed.

10 Claims, No Drawings

PREPARATION OF ADJUVANT-FREE FRUCTOSE TABLETS

BACKGROUND

The forming of powdered or granulated substances into coated and uncoated tablets constitutes a simple, valuable method of administrating such substances. Compression brings about a compaction which in many cases facilitates the delivery, storage and use of medicaments. One difficulty in the preparation of tablets lies in the fact that few substances can be directly compressed into tablets (cf. Gstirner, "Grundstoffe und Verfahren der Arzneibereitung," 1960, pp. 3–4). This is because most substances either are too sticky to permit smooth ejection of the tablets, or the substances cannot be bound together adequately by the pressures applied. A characteristic frequently encountered in many substances is that they stick to the tablet die to the punches, causing the tablets to be partially or completely pulled apart when the upper punch is raised. To circumvent these undesirable characteristics, adjuvants such as anti-adhesives, binders and parting agents are added in more or less great percentages to the ingredients used in the production of common tablets.

In a number of applications, however, the addition of tableting adjuvants is undesirable or impossible. For example, in the case of effervescent tablets the conventional adjuvants produce a certain degree of turbidity on account of their poor solubility in water. In the case of troches, however, the taste of the tableting adjuvants is often unpleasant. Other disadvantages may lie in a change in the dissolving speed of the tablet, in an adverse effect on the stability of the ingredients, and in the enlargement of the total mass of the tablet. In the case of medicaments and dietetic nutrients, the addition of adjuvants must be declared on the label according to law, and the consumer who sets great store by purity will steer clear even of harmless additives. Consequently, a number of attempts have been made to modify the prior-art tableting processes so as to enable tablets to be made without the addition of adjuvants.

It is known that tablets have less tendency to stick to the tablet die and to the punches if the tablets are compressed under very high pressures. The disadvantages of this method is that the tablet substances begin to sinter, so that the porosity of the tablet is destroyed, and very hard, poorly soluble tablets result, which also have a tendency to "cap" or split.

In one special process the contact surfaces of the punches are coated with a plastic substance to diminish adhesion forces and thus prevent sticking. Due to the high pressures required especially for the pressing of troches, however, these plastic surfaces are deformed relatively rapidly and ground away by the abrasive action of the substances being tableted. The resulting inaccuracy of tablet size and the necessary frequent replacement of the punches and dies militate against widespread technical use of this method.

Attempts have furthermore been made to utilize the movement of the lower punch for the purpose of lubricating the die walls with a liquid lubricant such as paraffin or silicone oil. The lubrication of the punch surfaces, however, cannot simultaneously be accomplished in this manner, so that, in spite of the great technical expense that is necessary, there are great difficulties involved in tableting by this method.

THE INVENTION

Surprisingly, we have succeeded in finding a method by which adjuvant-free tablets can be made without difficulty on conventional tableting machines, and by which the above-described disadvantages are also circumvented.

The method of the invention for preparing tablets from tableting masses having a tendency to stick to the punches and dies is characterized in that the pure tableting mass, and an adjuvant mass containing easily tableted substances, lubricants, and parting agents, are compressed alternately in each punch and die set.

Surprisingly, the pressing of the adjuvant substances leaves a thin coating of lubricant in the punches and dies, but one which is sufficient to assure the release of a residue-free and unbroken tablet upon the completion of the next pressing operation. The tablets made from the adjuvant mass can, of course, be crushed and reused in the process.

In an especially advantageous embodiment, a rotary press is used which has dual pressing stations, so that the adjuvant mass is being fed continuously to the one station and the tableting mass to the other.

Easily tableted substances for the adjuvant mass include, for example, sodium and potassium chloride, lactose, calcium phosphate, cellulose, starch, etc. Even though these substances will be found only in traces in the desired tablets, toxic or reactive substances will be avoided for reasons of safety.

Common substances such as talc or sodium benzoate can be used a lubricants, in about 5 to 20% by weight, preferably about 8 to 10%. Stearic acid and stearates in about 1 to 10%, preferably about 2 to 4%, have proven to be good mold parting agents. Mold parting or releasing agents of very good adhesion, such as paraffin or silicone oils, can produce the effect sought by the invention in amounts of as little as about 0.5 to 2%.

The pressures used in the process are relatively uncritical and are within the limits commonly used in tableting operations. The amount of tableting adjuvants in the adjuvant tablet, however, can be still further reduced if the pressing pressure at the station filled with these substances is lower than usual.

In accordance with this invention, therefore, tablets can for the first time be made from substances which have a tendency to stick to punches and dies, without the addition of parting agents or lubricants. Of course, these tablets may contain other desired adjuvants, such as additives to improve solubility and taste, such as sugar, acids and flavoring agents, or substances promoting the disintegration of the tablet, surfactants, buffers, or fillers such as starch and cellulose. Due to the lower press pressure which can be used in the process of the invention, the production especially of soft effervescent and sublingual tablets can be advantageously practiced.

We have also succeeded by our method in tableting pure fructose for the first time. Fructose, being a hygroscopic substance which is easily soluble in water, has hitherto been impossible to tablet without the addition of adjuvants. In accordance with the invention, however, it is possible to press granular or agglomerated fructose into tablets without additives. For larger tablets, or when the press pressure is not sufficient to crush the granules sufficiently, it is recommended that finely granulated or powdered fructose be added in about 10 to 30%, in order to produce sufficient tablet hardness without overstraining the tableting machine. The granulated fructoses containing no binding agent in accordance with West German Patent No. 1,909,316, however, can also be pressed without such an additive and are especially preferred.

EXAMPLES

The invention will now be explained with the aid of a number of examples of the composition of the adjuvant mass, and a number of examples of the tableting of sticky substances which has been accomplished by us.
Formulas for Adjuvant Masses

EXAMPLE 1

9.0 kg of lactose, crystalline, is uniformly mixed with 800 g of talc and 200 g of magnesium stearate.

EXAMPLE 2

8.0 kg of lactose, crystalline, 500 g of microcrystalline cellulose, 1.0 kg of talc and 500 g of magnesium stearate are uniformly mixed.

EXAMPLE 3

4.5 kg of lactose and 4.5 kg of cornstarch are granulated with a starch paste mixed with 100 g of silicone emulsion. 900 g of talc is then mixed with the dried and sifted granules.

EXAMPLE 4

100 g of paraffin is dissolved in a suitable solvent and absorbed into 1.5 kg of talc, then dried and sifted. This paraffined talc is uniformly mixed with 8.4 kg of spray-dried lactose.

EXAMPLE 5

8.5 kg of lactose, crystalline, 1.0 kg of macrocrystalline cellulose and 500 g of stearic acid are uniformly mixed.

EXAMPLE 6

9.5 kg of lactose, crystalline, is mixed uniformly with 500 g of magnesium stearate.
Formulas For Tableting Masses Containing Active Substances

EXAMPLE 7

5.0 kg of ascorbic acid, 12.5 kg of sodium hydrogen carbonate and 7.5 kg of anhydrous citric acid are granulated by conventional methods. On the one half of the tableting machine, 500 mg ascorbic acid effervescent tablets 22 mm in diameter and 2.5 g in weight, and on the other half a placebo tableting mass of Examples 1 or 2, are formed into tablets.

EXAMPLE 8

3.0 kg of acetylsalicylic acid, powdered, is granulated with a starch paste of 150 g of cornstarch, and dried and sifted. 600 g of microcrystalline cellulose is mixed with the granules. On the one half of the tableting machine, 300 mg acetylsalicylic acid tablets of 11 mm diameter and 375 mg weight are pressed, and on the other half a placebo tableting mass of Example 5 is pressed. The tablets containing the active substance can be pressed so soft that the tablets disintegrate very rapidly in water or in the mouth.

EXAMPLE 9

2.0 kg of polyethylene glycol 4000 and 250 g of polyhydroxyethylene stearate are heated to 60° C with fusion. 500 g of a micronized nitrofurantoin derivative is suspended in the melt. The solidified melt is crushed to granules of a size of 0.5 to 1.0 mm. On the one half of the tableting machine, 50 mg nitrofurantoin derivative tablets are made, of a diameter of 10 mm and a weight of 275 mg, and on the other half a placebo tableting mass of Example 6 is pressed. The tablets containing the active materials are then candy coated.

EXAMPLE 10

1.3 kg of lactose, powdered, and 1.3 kg of cornstarch are granulated with starch paste in the usual manner. The dried granules are coated with a solution of 3 g of peppermint oil in alcohol. The dried and sifted granules are uniformly mixed with a 5% nitroglycerine-lactose mixture. On the one half of the tableting machine, 0.5 mg nitroglycerine tablets are made, of 7 mm diameter and 140 mg weight, and on the second half a placebo tableting mass of Example 3 is pressed. The active material tablets are pressed so soft that they disintegrate very rapidly in the oral cavity.

EXAMPLE 11

5.5 kg of sorbitol and 1.5 kg of saccharin sodium are granulated together with a solution of alcohol and water. On the one half of the tableting machine, 15 mg of saccharin tablets of 6 mm diameter and 70 mg weight are made, and on the second half a placebo tableting mass of Example 1 or 2 is pressed.

EXAMPLE 12

7.5 kg of granulated fructose (prepared in accordance with West German Pat. No. 1,909.316) having a grain size of 0.2 to 0.5 mm, and 2,5 kg of granulated fructose (prepared in accordance with West German Pat. 1,909,316) and having a grain size of 0.05 to 0.2 mm, are mixed together. On the one half of the tableting machine, fructose troches are made having a diameter of 22 mm and a weight of 3.0 g, and on the second half a placebo tableting mass of Example 1, 2 or 3 is pressed.

While preferably one tablet of easily tableted material is formed after each tablet of sticky material, one could make two or three tablets of easily tableted material in sequence if it proved desirable. Similarly, if the nature of the sticky material permitted one could form several tablets from it between each formation of a tablet from the easily tableted material. In all instances, however, there would be a regular predetermined alternation of production of the two different tablets on the same machine and in the same mold cavities.

It will be appreciated that the instant specification and examples are set forth by way of illustration and not limitation, and that various modifications and changes may be made without departing from the spirit and scope of the present invention.

What is claimed is:
1. The method of preparing adjuvant-free tablets from a tableting mass having a tendency to stick, comprising alternately in the same mold forming tablets from said tableting mass and from an adjuvant mass containing an easily tableted substance, a lubricant and a mold parting agent.

2. The method of claim 1, wherein the lubricant comprises about 5 to 20% by weight of said adjuvant mass.

3. The method of claim 1, wherein the parting agent comprises about 0.5 to 10% by weight of said adjuvant mass.

4. The method of claim 1, wherein the tableting mass comprises substantially pure fructose.

5. The method of claim 4, wherein the tableting mass comprises by weight about 70 to 90% of fructose of a particle size larger than about 0.2 mm and about 10 to 30% of a particle size smaller than about 0.2 mm.

6. The method of claim 1, wherein said adjuvant by weight contains about 8 to 10% of said lubricant and about 1 to 4% of said parting agent.

7. The method of claim 6, wherein the process is performed on a rotary press having paired filling stations.

8. The method of claim 6, wherein the parting agent comprises about 0.5 to 10% by weight of said adjuvant mass.

9. The method of claim 8, wherein the process is performed on a rotary press having paired filling stations, and the easily tableted substance comprises at least one member selected from the group consisting of sodium chloride, potassium chloride, lactose, calcium phosphate, cellulose and starch, and the tablets from said adjuvant mass are crushed and recycled for production of further tablets.

10. A mass of uniform tablets of substantially pure fructose each comprises buy weight of about 100 parts by weight of particles larger than about 0.2 mm and about 10 to 30 parts by weight of particles smaller than about 0.2 mm.

* * * * *